(12) United States Patent
Nekoomaram et al.

(10) Patent No.: US 8,595,607 B2
(45) Date of Patent: Nov. 26, 2013

(54) METHOD AND SYSTEM FOR UPDATING A MEDICAL DEVICE

(75) Inventors: Saeed Nekoomaram, San Mateo, CA (US); Nathan Christopher Crouther, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 657 days.

(21) Appl. No.: 12/794,721

(22) Filed: Jun. 4, 2010

(65) Prior Publication Data

US 2010/0313105 A1    Dec. 9, 2010

Related U.S. Application Data

(60) Provisional application No. 61/184,234, filed on Jun. 4, 2009.

(51) Int. Cl.
G06F 11/10    (2006.01)

(52) U.S. Cl.
USPC .......................................... 714/807

(58) Field of Classification Search
USPC .......... 714/708, 758, 710, 701, 799; 717/171; 709/221
See application file for complete search history.

(56) References Cited

U.S. PATENT DOCUMENTS

| | | | |
|---|---|---|---|
| 6,445,462 B2 | 9/2002 | Aritomi | |
| 6,694,191 B2 | 2/2004 | Starkweather et al. | |
| 7,120,858 B2 * | 10/2006 | Zak et al. | 714/807 |
| 7,178,141 B2 | 2/2007 | Piazza | |
| 7,185,262 B2 * | 2/2007 | Barthel et al. | 714/758 |
| 7,321,811 B1 | 1/2008 | Rawls-Meehan | |
| 7,523,350 B2 * | 4/2009 | Lintz et al. | 714/36 |
| 7,711,989 B2 * | 5/2010 | Wang et al. | 714/36 |
| 7,774,145 B2 | 8/2010 | Brauker et al. | |
| 7,779,183 B2 | 8/2010 | Koehler et al. | |
| 8,117,481 B2 | 2/2012 | Anselmi et al. | |
| 8,285,386 B2 | 10/2012 | Crivelli et al. | |
| 2003/0208465 A1 | 11/2003 | Yurko et al. | |
| 2006/0010098 A1 | 1/2006 | Goodnow et al. | |

(Continued)

FOREIGN PATENT DOCUMENTS

EP    1248661    8/2012

OTHER PUBLICATIONS

PCT Application No. PCT/US2010/037547, International Preliminary Report on Patentability and Written Opinion of the International Searching Authority mailed Dec. 15, 2011.

(Continued)

*Primary Examiner* — Phung M Chung
(74) *Attorney, Agent, or Firm* — Jackson & Co., LLP.

(57) ABSTRACT

The present disclosure includes methods, devices and systems for establishing a connection between a medical device and a remote computing device, receiving an upgrade command at the medical device, storing a current version of persistent data and a current version of executable code in a first storage area of the medical device, transmitting at least the current version of the persistent data to the remote computing device, receiving a second format of the current version of the persistent data and an upgraded version of executable code at the medical device, storing the second format of the current version of the persistent data and the upgraded version of the executable code in a second storage area of the medical device, and executing the upgraded version of the executable code with the second format of the current version of the persistent data.

52 Claims, 8 Drawing Sheets

(56) References Cited

U.S. PATENT DOCUMENTS

| | | |
|---|---|---|
| 2006/0173644 A1 | 8/2006 | Dai et al. |
| 2007/0027506 A1 | 2/2007 | Stender et al. |
| 2007/0192140 A1 | 8/2007 | Gropper |
| 2007/0255114 A1 | 11/2007 | Ackermann et al. |
| 2007/0255348 A1* | 11/2007 | Holtzclaw .................. 607/60 |
| 2008/0301158 A1 | 12/2008 | Brown et al. |
| 2008/0301665 A1 | 12/2008 | Charlton et al. |
| 2009/0099864 A1 | 4/2009 | Cronrath et al. |
| 2009/0150865 A1 | 6/2009 | Young et al. |
| 2009/0192724 A1 | 7/2009 | Brauker et al. |
| 2010/0261987 A1 | 10/2010 | Kamath et al. |
| 2011/0320130 A1 | 12/2011 | Valdes et al. |
| 2012/0096451 A1 | 4/2012 | Tenbarge et al. |
| 2012/0165614 A1 | 6/2012 | Strickland et al. |

OTHER PUBLICATIONS

PCT Application No. PCT/US2010/037547, International Search Report and Written Opinion of the International Searching Authority mailed Jul. 27, 2010.

* cited by examiner

| Device Software | First Microprocessor | Second Microprocessor | Third Microprocessor |
|---|---|---|---|
| Release 10 | Release 10 | Release 8 | Release 6 |
| Release 14 | Release 12 | Release 8 | Release 7 |
| Release 15 | Release 12 | Release 8 | Release 7 |

FIG. 6

METHOD AND SYSTEM FOR UPDATING A MEDICAL DEVICE

RELATED APPLICATION

The present application claims priority under 35 U.S.C. §119(e) to U.S. Provisional Patent Application No. 61/184,234, entitled "Failure Recovery Methods of Corrupted Device Or During Software Downloads and Preservation of User Data and Manufacturing Data", filed on Jun. 4, 2009, the disclosure of which is incorporated herein by reference in its entirety for all purposes.

BACKGROUND

In diabetes management, devices are available for diabetic patients to measure their blood glucose levels. One such type of device is a continuous glucose monitoring device that periodically receives and processes analyte related data from a transcutaneous sensor. The received and processed data may then be output on a display of the continuous blood glucose monitoring device or otherwise provided to the patient to enable the patient to continuously track measured glucose levels.

One challenge of currently available continuous glucose monitoring devices is upgrading software or firmware of the continuous glucose monitoring devices and the components of the continuous glucose monitoring devices. Further, if a patient experiences a problem with a continuous glucose monitoring device, such as, for example, the continuous glucose monitoring device ceases to function or data in the continuous glucose monitoring device becomes corrupt, the settings and/or the analyte related data stored on the continuous glucose monitoring device may be lost. Further, if a patient switches from using one continuous glucose monitoring device to another continuous glucose monitoring device, the user may need to manually change factory default settings of the new continuous glucose monitoring device to match the settings of the old continuous glucose monitoring device, which can be a time consuming process.

SUMMARY

Embodiments described herein include methods and/or systems for updating a medical device and recovering from a failure to upgrade the medical device. In certain embodiments, a connection is established between a medical device and a remote computing device. An upgrade command is received at the medical device and in response to the upgrade command the medical device stores a current version of persistent data and a current version of executable code in a first storage area of the medical device. The medical device then transmits at least the current version of the persistent data to the remote computing device. The remote computing device is configured to convert the current version of the persistent data from a first format to a second format, with the first format of the current version of the persistent data corresponding to the current version of executable code and the second format of the current version of the persistent data corresponding to an upgraded version of executable code. The medical device receives the second format of the current version of the persistent data and the upgraded version of the executable code, stores the second format of the current version of the persistent data and the upgraded version of the executable code in a second storage area, and executes the upgraded version of the executable code and the second format of the current version of the persistent data in place of the current version of the executable code and the first format of the current version of the persistent data.

These and other objects, features and advantages of the present disclosure will become more fully apparent from the following detailed description of the embodiments, the appended claims and the accompanying drawings.

INCORPORATED BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,356,786; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,041,468; 7,167,818; and 7,299,082; U.S. Published Application Nos. 2004/0186365; 2005/0182306; 2006/0025662; 2006/0091006; 2007/0056858; 2007/0068807; 2007/0095661; 2007/0108048; 2007/0199818; 2007/0227911; 2007/0233013; 2008/0066305; 2008/0081977; 2008/0102441; 2008/0148873; 2008/0161666; 2008/0267823; and 2009/0054748; U.S. patent application Ser. Nos. 11/461,725; 12/131,012; 12/242,823; 12/363,712; 12/495,709; and 12/698,124; and 12/714,439 and U.S. Provisional Application Ser. Nos. 61/184,234; 61/230,686; 61/227,967; 61/347,754; and 61/347,813.

BRIEF DESCRIPTION OF THE DRAWINGS

FIG. 6 illustrates an exemplary compatibility table according to embodiments of the present disclosure;

DETAILED DESCRIPTION

Figure 1:
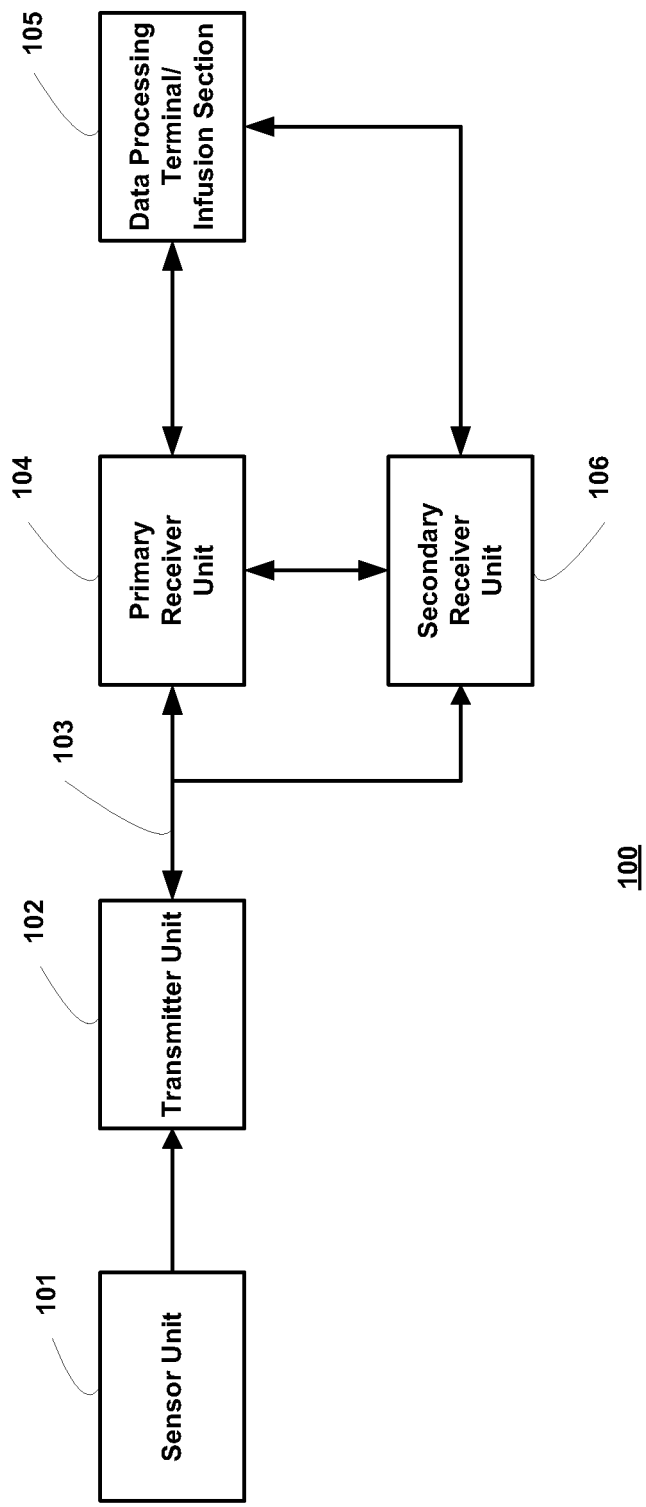
FIG. 1 illustrates a block diagram of a data monitoring and management system according to embodiments of the present disclosure.

Before the present disclosure is described in additional detail, it is to be understood that this disclosure is not limited to particular embodiments described, as such may, of course, vary. It is also to be understood that the terminology used herein is for the purpose of describing particular embodi-} ments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Embodiments described herein relate to upgrading, updating, adding, or modifying a medical device such as, for example, a continuous glucose monitoring device, and/or components of an analyte monitoring system. In certain aspects of the present disclosure, the device is upgraded and provided with updated software and/or data to assist users in better managing their health. In the manner described, in aspects of the present disclosure, patients with Type-1 or Type-2 diabetic conditions may improve their diabetes management, and further, the patients, users or healthcare providers may be provided with tools to improve the treatment of such conditions.

Software and firmware upgrades and the methods described herein may be used with various components of a data monitoring and management system such as the data monitoring and management system 100 illustrated in FIG. 1. In certain embodiments, the data management and monitoring system 100 is an analyte monitoring and management system, such as a continuous glucose monitoring management system. Although a continuous glucose monitoring system is specifically mentioned, it is contemplated that features described herein may also be applicable to other medical monitoring devices such as drug or medication delivery devices and the like.

Referring back to FIG. 1, the analyte monitoring system 100 includes a sensor unit 101, a data processing and/or communication unit such as, for example, a transmitter unit 102 coupleable to the sensor unit 101, and a primary receiver unit 104 which is configured to communicate with the transmitter unit 102 via a bi-directional communication link 103. In certain embodiments, the communication link 103 may include an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

Although not shown, it is contemplated that the sensor unit 101 and the transmitter unit 102 may be configured as a single integrated unit such as an on body patch device. In such embodiments, the integrated unit may wirelessly communicate with other components of the system 100 such as described herein.

The primary receiver unit 104 may be further configured to transmit data to a data processing terminal 105 for evaluating the data received by the primary receiver unit 104. Moreover, the data processing terminal 105 in one embodiment may be configured to receive data directly from the transmitter unit 102 via a communication link which may optionally be configured for bi-directional communication. Accordingly, transmitter unit 102 and/or receiver unit 104 may include a transceiver.

Also shown in FIG. 1 is an optional secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bidirectional wireless communication with each or one of the transmitter unit 102, the primary receiver unit 104 and the data processing terminal 105. In one embodiment of the present disclosure, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, pager, mobile phone, PDA, for example. In certain embodiments, the secondary receiver unit 106 may be configured with the same or substantially similar functionality as the primary receiver unit 104. Each receiver unit may be configured to be used in conjunction with a docking cradle unit, for example for one or more of the following or other functions: placement by bedside, for recharging, for data management, for night time monitoring, and/or bidirectional communication device.

In one aspect, sensor unit 101 may include two or more sensors, each configured to communicate with transmitter unit 102. Furthermore, only one, transmitter unit 102, communication link 103, and data processing terminal 105 are shown in the embodiment of the monitoring system 100 illustrated in FIG. 1. However, it will be appreciated by one of ordinary skill in the art that the analyte monitoring system 100 may include one or more sensors, multiple transmitter units 102, communication links 103, and data processing terminals 105. Moreover, within the scope of the present disclosure, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present disclosure, the sensor unit 101 is physically positioned in or on the body of a user whose analyte level is being monitored. The sensor unit 101 may be configured to continuously sample the analyte level of the user and convert the sampled analyte level into a corresponding data signal for transmission by the transmitter unit 102. In certain embodiments, the transmitter unit 102 may be physically coupled to the sensor unit 101 so that both devices are integrated in a single housing and positioned on the user's body. The transmitter unit 102 may perform data processing such as filtering and encoding on data signals and/or other functions, each of which corresponds to a sampled analyte level of the user, and in any event transmitter unit 102 transmits analyte information to the primary receiver unit 104 via the communication link 103. Additional detailed description of the continuous analyte monitoring system and its various components are provided in but not limited to: U.S. Pat. Nos. 6,134,461, 6,175,752, 6,121,611, 6,560,471, 6,746,582, and U.S. Patent Publication No. 2008/0278332 filed May 8, 2008 and elsewhere, the disclosure of each of which are incorporated by reference for all purposes.

Figure 2:
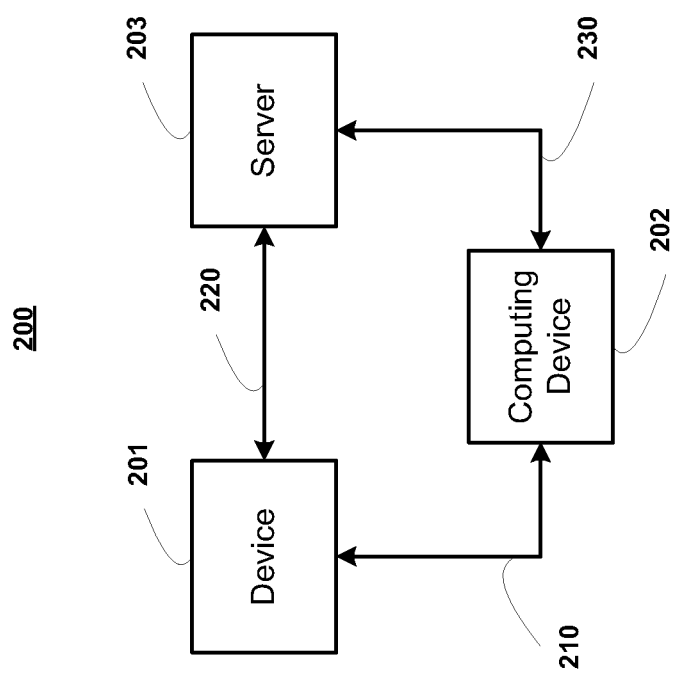
FIG. 2 illustrates a block diagram of an upgrade and recovery system according to embodiments of the present disclosure.

FIG. 2 illustrates a block diagram of an upgrade and recovery system 200 according to embodiments of the present disclosure. In certain embodiments, the upgrade and recovery system 200 includes, but is not limited to, a device 201, a computing device 202, and a server 203. As will be appreciated by one of ordinary skill in the art, the upgrade recovery system 200 may be used with the various components of the data monitoring and management system 100 (FIG. 1). As such, as used herein, the term device, such as device 201 for example, may refer to a medical device, the transmitter unit 102, the primary receiver unit 104, and/or the secondary receiver unit 106.

In certain embodiments, the device 201 includes a plurality of microprocessors. Non-limiting examples include an ARM9 microprocessor, a MSP430 microprocessor, and a CC2510 microprocessor. In one aspect, at least one microprocessor of the device 201, such as, for example, an ARM9 microprocessor, is configured to handle user interface functionalities of the device 201, store persistent data (e.g. manufacturing setting and user-configurable settings) corresponding to the device 201, and store and manage the software and software upgrades for the other microprocessors (e.g., the MSP430 microprocessor and the CC2510 microprocessor) of the device 201. For example, when software corresponding to the MSP430 microprocessor is upgraded, the upgraded version of the software for the MSP430 microprocessor is stored in the ARM9 microprocessor. Thus, when the device 201 boots, a bootloader of the ARM9 microprocessor loads the software for the ARM9 microprocessor, the software for the CC2510 microprocessor and the upgraded version of the software for the MSP430 microprocessor.

In certain embodiments, a second microprocessor of the device 201, such as, for example, a MSP430 microprocessor, is configured to process glucose readings from a test strip inserted into the device 201 and/or manage continuous glucose data received from a sensor, such as, for example sensor unit 101 (FIG. 1). In another embodiment, a third microprocessor of the device, such as, for example a CC2510 microprocessor, is configured to interface with various peripheral devices, such as, for example, a wireless pump. Thus, using the third microprocessor of the device 201 a user may control the peripheral device directly from the device 201. Although specific microprocessors have been discussed, it is contemplated that various other microprocessors may be used by the device 201.

In certain embodiments, the computing device 202 may be a user's personal computer or laptop. The computing device 202 may also be a personal digital assistant, smart phone, tablet computer or other portable computing device that may receive data from the device 201 or transfer data to the device 201. The computing device 202 may be configured to store and/or further analyze data, such as, for example, blood glucose data and/or continuously monitored glucose data from the device 201 that was transferred to the computing device 202 via a wireless or wired connection. In certain embodiments, a web-based application or other client application may be stored in a memory of the computing device 202 and may be executed by one or more processors of the computing device 202. Such applications may enable a user to view analyte related data on the computing device 202 as well as viewing and downloading available software and firmware upgrades for the device 201.

In certain embodiments, server 203 is configured to provide upgrades for the device 201 and/or the computing device 202. The upgrades for the device 201 and the computing device 202 include software upgrades, data upgrades, and firmware upgrades. The server 203 is further configured to store and/or analyze and process data obtained from device 201 and computing device 202 and transmit the received data to another computing device (not shown) such as, for example, a computing device of a healthcare provider.

In certain embodiments, the server 203 includes a database or other such data structure that stores serial numbers corresponding to a plurality of devices. The database also stores a compatibility table that corresponds to each device. As will be explained in greater detail below, the compatibility table associated with each device is used to store and track versions of software and firmware that have been downloaded and installed on the device 201 as well as user-configurable data associated with each version of software installed on the device 201. In one aspect, the compatibility table also stores information corresponding to the hardware versions of each of the microprocessors of the device 201 as well as software/firmware versions for each of the microprocessors of the device 201.

Referring back to FIG. 2, in certain embodiments, communication links 210, 220, and 230 connect the device 201 and computing device 202; the device 201 and the server 203; and the computing device 202 and the server 203. The communication links 210, 220, and 230 may include one or more of an RF communication protocol, an infrared communication protocol, a Bluetooth® enabled communication protocol, an 802.11x wireless communication protocol, a Zigbee communication protocol, and the like.

One or more components of the upgrade and recovery system 200 may function to perform various and multiple upgrade and recovery operations related to software and data upgrades, data recovery, and/or data preservation. In certain embodiments, the upgrade and recovery system 200 may perform one or more routines for downloading data to a device, such as device 201 as described below in conjunction with the method 300 of FIG. 3.

Figure 3:
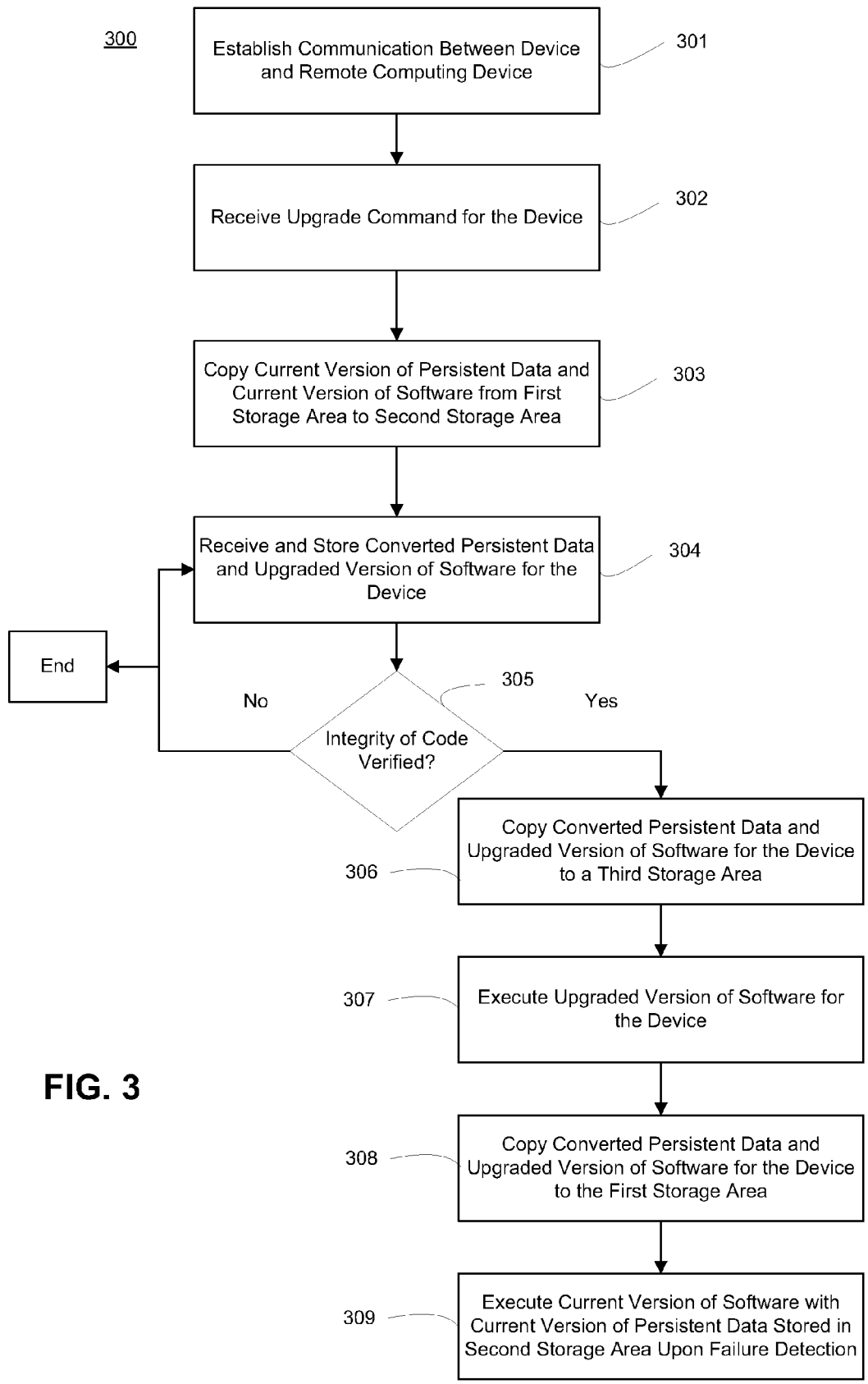
FIG. 3 is a flowchart illustrating a method for updating a medical device according to embodiments of the present disclosure.

Referring to FIG. 3, communication between a device, such as device 201 (FIG. 2), and at least one remote computing device, such as computing device 202 or server 203, is established (301). In certain embodiments, communication between the device 201 and the remote computing device is established through communication links 210 or 220. In one aspect, the communication between the device 201 and the remote computing device is established using a wireless connection. In another aspect, the communication between the device 201 and the remote computing device is established using a wired connection such as, for example, by connecting the device 201 to the remote computing device using a USB cable.

In certain embodiments, the device 201 includes a first memory for storing instructions for execution by the one or more microprocessors of the device 201 to upgrade, for example, software algorithms, computer executable routines and/or any other types of executable code stored on the device 201. The executable code may be written in one or more machine readable languages for retrieval and execution by one or more microprocessor driven or microprocessor controlled components of the device 201. For example, the upgrades may correspond to upgrades for an operating system being executed on the device 201, an application (e.g., bolus calculator application) being executed on the device 201 that enhances the functionality of the device 201, an application programming interface (API) (e.g., applications for communicating with and/or controlling peripheral devices that have been connected to the device 201) being executed on the device 201, and the like. Further, in certain embodiments, the instructions for execution by the one or more microprocessors of the device 201 are configured to verify the integrity of the upgraded version of the software algorithms, computer executable routines and/or the other executable code for the device 201. In another embodiment, the instructions for execution by the one or more microprocessors of the device 201 are configured to verify the integrity of user-configurable data and manufacturing data that will be used by the upgraded version of the software algorithms, computer executable routines and/or other executable code for the device 201. In certain embodiments, the user-configurable data corresponds to user settings of the device 201 such as, for example, glucose threshold values, alarm settings, reminder settings, and language settings. In certain embodiments, the manufacturing data may include data that is used to identify the device 201 such as, for example, a serial number of the device 201. Additionally, the manufacturing data may also include default settings for the device 201 (e.g. unit of measure, an analog to digital converter (ADC) count etc.) and/or a current version of software that is being executed by the device 201.

The device 201 further includes a second memory with a plurality of segregated areas for storage of various types data (e.g., user-configurable data and upgraded versions of the user-configurable data) or upgraded versions of the software for the device 201. In certain embodiments, the first and/or second memory is random access memory. In another embodiment, the first memory is volatile memory. In yet another embodiment, the second memory is non-volatile memory, which may be flash memory. In certain embodiments, the first memory and the second memory are non-volatile or flash memory.

In certain embodiments, software that is executed by a microprocessor of the device 201 (e.g., a current version of the software or a current version of executable code), as well as the user-configurable and manufacturing data utilized by the software that is executed by the microprocessor of the device 201, is stored in a first storage area of the second memory of the device 201. For example, the software that is executed by a microprocessor of the device 201 may be an operating system of the device 201, an application utilized by the operating system to enhance the functionality of the device 201, or an application programming interface of the device 201. In one aspect, the user-configurable data and the manufacturing data is stored in a memory of the device 201 so that the user-configurable data and the manufacturing data may be used to restore the settings of the device 201 should any problems occur with the device 201, such as, for example, the device 201 becoming disconnected from the server 203 or the computing device 202 during the upgrade process, by upgrade not being fully installed on the device 201, or if the upgrade installed on the device 201 is corrupt or is not compatible with the device 201. If a problem occurs when upgrading the device 201, the user-configurable data and manufacturing data may be used to restore the stored settings of the device 201.

Referring still to FIG. 3, in certain embodiments, the device 201 (FIG. 2) receives a command from a remote computing device regarding the download of an upgrade that is to be processed at the device 201 (302). In certain embodiments, the upgrade for the device 201 may be an upgrade to software currently being executed on the device 201, a new application programming interface (API) for the device 201, an upgrade to firmware for the device 201, or a new software application for the device 201. In certain embodiments, the upgrade command is initiated by the remote computing device and communicated by the remote computing device, such as, for example, the computing device 202, to the device 201. In certain embodiments, a microprocessor of the device 201 automatically initiates installation or downloading of the upgrade directly from the remote computing device when the command is received from the remote computing device. In another embodiment, the download of the upgrade for the device 201 will not be initiated until a user confirms that the available upgrade for the device 201 is desired.

When the download of the upgrade is initiated, the existing user-configurable data and manufacturing data (e.g., persistent data) utilized by the version of the software being executed by the device 201 (e.g., the user-configurable data and manufacturing data stored in the first memory area of the second memory of the device 201) is packed and copied along with the version of the software being executed on the device 201, to a second storage area of the second memory of the device 201 (303). In certain embodiments, the persistent data is packed or compressed using an encoding scheme (e.g., lossy or lossless encoding scheme) so that the persistent data may be represented using fewer bits than if the persistent data was not packed or compressed. Because the data is compressed, memory space of the device 201 may be conserved. Further, because the packed persistent data (e.g., user-configurable data and manufacturing data) is represented by a fewer number of bits, bandwidth requirements for transferring the packed persistent data from the device 201 to the remote computing device may also be reduced (e.g., the amount of bandwidth required to transmit the packed persistent data is less than the amount of bandwidth required to transmit persistent data that has not been packed). Once the persistent data is packed, the persistent data may then be uploaded to the remote computing device, such as, for example a computing device 202 executing a software upgrade module. The persistent data may then be uploaded from the computing device 202 to the server 203. In one aspect, the packed persistent data may be uploaded directly from the device 201 to the server 203.

Once the packed persistent data has been uploaded to the server 203, the server 203 unpacks the persistent data and converts the persistent data to a new version of persistent data that can be utilized by the upgraded version of the software for the device 201 that is to be downloaded to the device 201 during the upgrade process. Once the persistent data has been converted by the server 203, the new version of persistent data is packed (e.g. compressed) by the server 203 and downloaded to the device 201, along with the upgraded version of the software, and is stored in the first memory of the device 201 (304).

In certain embodiments, when the conversion of the persistent data is performed by the server 203, the persistent data is mapped to a new version of persistent data so that the settings utilized by the user in the previous software version (e.g., the version of the software that was executed on the device 201 prior to the upgrade) are maintained by the upgraded version of the software that is to be installed on the device 201. Mapping of the persistent data will be described in more detail below with respect to FIG. 5.

In certain embodiments, the server 203 performs the upload, conversion, and download through client software being executed on the server 203. In another embodiment, the upload, conversion and download of the persistent data and upgraded version of the software for the device 201 is performed through an upgrade module being executed on an intervening device, such as, for example, the computing device 202. In another embodiment, the conversion may be performed directly on the device 201.

Once the new version of the persistent data and the upgraded version of the software have been downloaded to the device 201 and stored in the first memory of the device 201, the integrity of the new version of the persistent data as well as the integrity of the upgraded version of the software for the device 201, is verified (305). In certain embodiments, verification of the new version of the persistent data and verification of the upgraded version of the software for the device 201 includes confirmation that the new version of the persistent data and the upgraded version of the software for the device 201 are not corrupt (e.g., no errors occurred in the transmission of the new version of the persistent data or the upgraded version of the software for the device 201 from the server to the second device) or that the new version of the persistent data and the upgraded version of the software may be used by the device 201. In certain embodiments, the integrity verification is performed by cyclic redundancy check (CRC). Thus, as the data is sent from the server 203 to the device 201, a CRC code is generated for each block of data. The CRC code is sent with each block of data and received by the device 201. When the block of data is received and/or read by a microprocessor of the device 201, the device 201 generates a CRC code for each received block of data and compares the generated CRC code with the received CRC code. If the CRC codes match, the data is verified. If however, the CRC codes do not match, a data error is detected. Although a cyclic redundancy check is specifically mentioned, it is contemplated that other error detection methods may be used including using parity bits, checksums, cryptographic hash functions and the like.

If the verification of the new version of the persistent data and the upgraded version of the software is satisfactory (e.g., no errors were detected by the cyclic redundancy check), the new version of the persistent data and the upgraded version of the software for the device 201 are copied from the first memory of the device 201 to a third storage area of the second memory of the device 201 (306).

In certain embodiments, if the new version of the persistent data and the upgraded version of the software for the device 201 are not verified by the cyclic redundancy check (e.g., the data is corrupt) (305) the method 300 ends and the user is notified that the upgrade was not completed. In certain embodiments, the user may be notified by a display screen output on a display of the device 201 that the upgrade to the software of the device 201 was not successful. Such errors may be caused by the device 201 becoming disconnected from the remote computing device or by a data transmission error (e.g. dropped data packets) between the server 203 and the device 201. In certain embodiments, if the new version of the persistent data and the upgraded version of the software for the device 201 is not verified, the new version of the persistent data and the upgraded version of the software for the device 201 is neither stored in the first memory of the device 201 or the second memory of the device 201.

In certain embodiments, if the integrity of the new version of the persistent data and the upgraded version of the software for the device 201 is not verified (305) the new version of persistent data, along with the upgraded version of the software for the device is downloaded from the server 203 to the device 201 a second time and stored in the first memory of the device 201 (304). In one aspect, if one portion of the data is verified, but another portion of the data is not verified, the unverified portion of the data is downloaded from the server 203 a second time while the verified portion of the data from the first download is stored in the first memory of the device 201.

For example, if the new version of the persistent data is verified by the cyclic redundancy check but the upgraded version of the software for the device 201 is not verified by the cyclic redundancy check, only the upgraded version of the software for the device 201 is downloaded a second time. Once the upgraded version of the software for the device 201 has been downloaded the second time, the integrity of the upgraded version of the software for the device 201 is verified (305). When both the new version of the persistent data and the upgraded version of the software for the device 201 have been verified, the new version of the persistent data and the upgraded version of the software for the device 201 are copied from the first memory of the device 201 to a third storage area of the second memory of the device 201 (306).

When the new version of the persistent data and the upgraded version of the software for the device 201 have been copied from the first memory of the device 201 to the third storage area of the second memory of the device 201, in certain embodiments, a microprocessor of the device 201 initiates a reset command to reset the device 201. Once the reset is complete, the microprocessor of the device 201 attempts to execute the upgraded version of the software for the device 201 and utilize the new version of the persistent data (307). As the microprocessor of the device 201 is executing the upgraded version of the software for the device 201 and utilizing the new version of the persistent data, the packed new version of the persistent data and the upgraded version of the software for the device 201 that is stored in the third storage area of the second memory of the device 201 is unpacked and stored in the first storage area of the second memory of the device 201 (308). In certain embodiments, the new version of the persistent data and/or upgraded version of the software for the device 201 is unpacked or decompressed such that the data is reconstructed in a form, or in a substantially similar form, as it was prior to the data being packed or compressed. For example, if a language setting of the persistent data was represented by 4 bits prior to being compressed, and was represented by 2 bits after being compressed, when the persistent data is subsequently decompressed, the language setting of the persistent data is once again represented by 4 bits.

If a failure occurs while copying the new version of the persistent data and the upgraded version of the software for the device 201 from the third storage area of the second memory to the first storage area of the second memory, the copying process stops and the microprocessor of the device 201 initiates a reset command. When the device 201 recovers from the reset, a bootloader of the device 201 loads the persistent data and the version of the software (e.g., the version of the software of the device 201 prior to the upgraded version of the software for the device 201) that is stored in the second storage area of the second memory of the device 201 (309) and the microprocessor of the device executes the loaded version of the software. When the device 201 boots executing the software version that was stored on the second storage area of the second memory of the device 201, the microprocessor of the device 201 re-initiates the upgrade process. In one aspect, when the device 201 boots executing the software version that was stored on the second storage area of the second memory of the device 201, the user may be prompted, via a display screen on the device 201, to re-initiate installation of the upgraded version of the software for the device 201.

In certain embodiments, upon successful installation of the upgraded version of the software for the device 201, the new version of the persistent data and the upgraded version of the software for the device 201 are copied from the third storage area of the second memory of the device 201 to the second storage area of the second memory of the device 201. Thus, the device 201 will have a backup copy of the upgraded version of the software for the device 201 and a copy of the new version of the persistent data stored in memory should the device 201 need to recover from a system failure.

In other embodiments, the new version of the persistent data and the upgraded version of the software for the device 201 may be copied from the first memory of the device 201 directly to the first storage area of the second memory of the device 201. The new version of the persistent data and the upgraded version of the software for the device 201 is executed and installed on the device 201 and upon successful installation, the new version of the persistent data and the upgraded version of the software for the device 201 may be copied to the second storage area of the second memory of the device 201 to serve as a backup copy of the upgraded version of the software for the device 201 and the new version of the persistent data.

In some embodiments of the present disclosure, method 300 may be applied as an upgrade method for various types of upgrades including, but not limited to, firmware upgrades, software patches, protocol updates, and any other executable code upgrades, patches or new versions.

In certain embodiments, the upgraded version of the software for the device 201 may correspond to a critical update for the device 201. In one aspect, if the critical update is not installed on the device 201, the device 201 may not function properly. For example, the critical update may correspond to a bolus calculation function or bolus delivery function of peripheral pump connected to the device 201. If the critical update is not installed on the device 201, an incorrect bolus dosage may be calculated and/or the pump may not deliver the expected amount of insulin based on the calculation.

In certain aspects, if a failure occurs during the installation of the critical update on the device 201, the microprocessor of the device 201 initiates a reset command and the device 201 resets. When the device 201 recovers from the reset, the microprocessor of the device 201 may cause the download and/or installation of the critical update to automatically restart. In certain embodiments, when the device 201 recovers from the reset, the user of the device 201 may be prompted to reinitiate the download and/or installation of the critical update. The prompt may be a message screen output on a display of the device 201, an audible alert, a tactile alert or a combination thereof.

In certain embodiments, when the device 201 recovers from the reset, the bootloader of the device 201 loads the persistent data and the version of the software (e.g., the version of the software of the device 201 prior to the upgraded version of the software for the device 201) that is stored in the second storage area of the second memory of the device 201 as was described above. However, in one aspect, the functionality or feature of the device 201 that corresponds to the critical update will not be accessible by the user until the critical update is installed. For example, if the critical update corresponds to a bolus calculation function, the user may not use the bolus calculation function until the critical update corresponding to the bolus calculation function is installed on the device 201. Although the particular functionality of the device 201 corresponding to the critical update is not operational, other features and functionalities of the device 201 are not affected. For example, although a bolus calculation function is not accessible by the user, a test strip port and blood glucose calculation function may be operational on the device 201.

It is also contemplated that although the critical update may correspond to a particular feature of the device 201, all functionalities and features of the device 201 may be nonfunctional until the critical update is installed on the device 201. In such cases, a message or alert screen may be output on the display of the device 201 indicating that all features and functionalities of the device 201 are non-functional and will remain non-functional until the critical update has been installed on the device 201. The user may then be prompted to reinitiate the download and/or installation of the critical update.

In yet another aspect, the functionality of the device 201 that corresponds to the critical update may have limited operational capabilities for a predetermined amount of time. For example, if the critical update corresponds to medication delivery of a peripheral pump, the microprocessor of the device 201 may instruct the peripheral pump to deliver a predetermined amount of insulin for the predetermined amount of time. When the predetermined amount of time expires, the user may be prompted to re-initiate the download and/or installation of the critical update.

Figure 4:
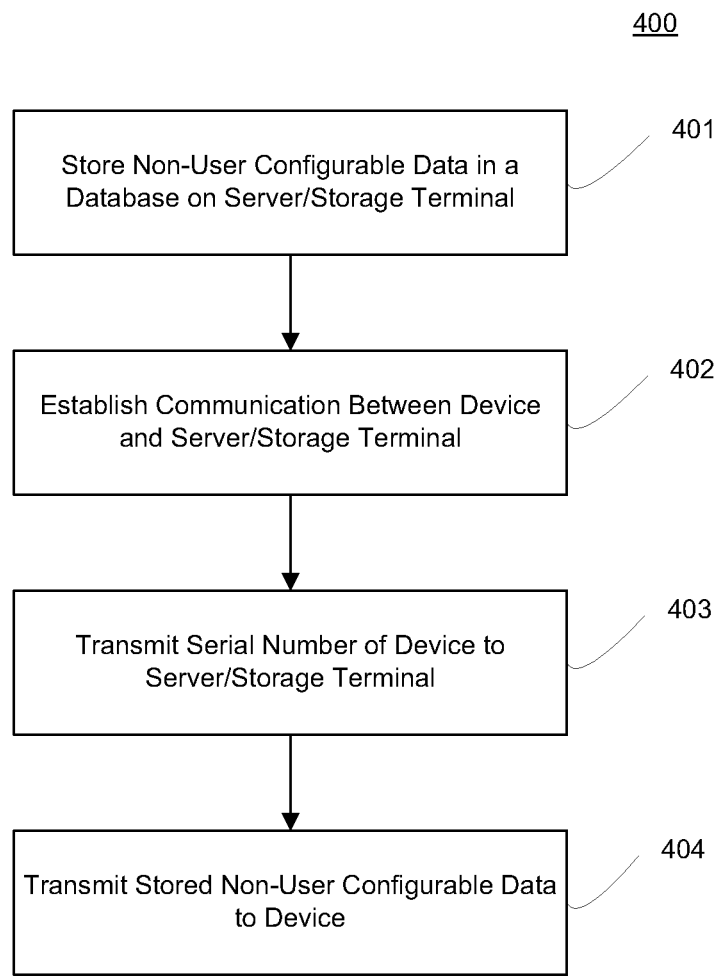
FIG. 4 is a flowchart illustrating a method for recovering non-user configurable data according to embodiments of the present disclosure.

FIG. 4 is a flow chart illustrating a method 400 for use in one or more embodiments of the present disclosure, for recovering non-user configurable data (e.g., manufacturing data) used by a device, such as, for example device 201 (FIG. 2), in which the non-user configurable data has been corrupted or is no longer stored on the device 201. Referring to FIG. 4, the non-user configurable data, which is specific to the device 201, is stored in a database on a remote computing device, such as, for example, a server 203, a data storage terminal, or other computing device, such as, for example, computing device 202 (401). In certain embodiments, the non-user configurable data may be uploaded and stored on the remote computing device at predetermined times (e.g., every 3 months) or each time the device 201 is connected either directly or indirectly to the remote computing device. In another embodiment, the non-user configurable data is uploaded and stored on the remote computing device prior to a user initiated software upgrade. As discussed above, the non-user configurable data is associated with a serial number that identifies the device 201, a version of software being executed on the device 201 and/or default settings of the device 201.

Still referring to FIG. 4, electronic communication between the remote computing device and the device 201 is established (402) and the serial number for the device 201 is transmitted to the remote computing device (403). Such transmission may be initiated by a user of the device 201 upon experiencing, for example, a malfunction or problem with the device 201. In certain embodiments, the user provides the serial number through a user interface of the device 201 or through a user interface on a computing device that is in communication with the device 201. In certain embodiments, the microprocessor of the device 201 causes the serial number of the device 201 to be automatically transmitted to the remote computing device when a connection between the device 201 and the remote computing device is established. Further, the microprocessor of the device 201 may be configured to transmit the serial number to the remote computing device when a connection between the remote computing device and the device 201 is established if various performance indicators (e.g., a failure or partial failure of the device 201 or components of the device 201) are detected by the microprocessor of the device 201.

Upon receipt of the serial number, remote computing device transmits the stored non-user configurable data to the device 201 (404). As will be described in detail below, the non-user configurable data may be stored in a compatibility table, such as, for example compatibility table 600 (FIG. 6). The transmission of the non-user configurable data from the remote computing device to the device 201 may be automatically performed in response to the receipt of the serial number, as receipt of the serial number at the remote computing device, for example, may indicate that the device 201 experienced a malfunction and requires the non-user configurable data to restore functionality of the device 201. In certain embodiments, transmission of the stored non-user configurable data may be transmitted from the remote computing device when the serial number is received in conjunction with a request from the user to transmit the non-user configurable data from the server 203 to the device 201.

In certain embodiments, the non-user configurable data may identify the device 201 and include default settings for the device 201 or the settings for the device 201 based on the version of the software that was last installed on the device 201. When the non-user configurable data for the identified device 201 has been transmitted to the device 201, the device 201 may use the non-user configurable data to restore the device settings of the device 201 to the settings that were used prior to the operational problems of the device 201. In certain embodiments, when the non-user configurable data is transmitted to the device 201 from the remote computing device, the non-user configurable data is stored in a memory of the device 201.

Figure 5:
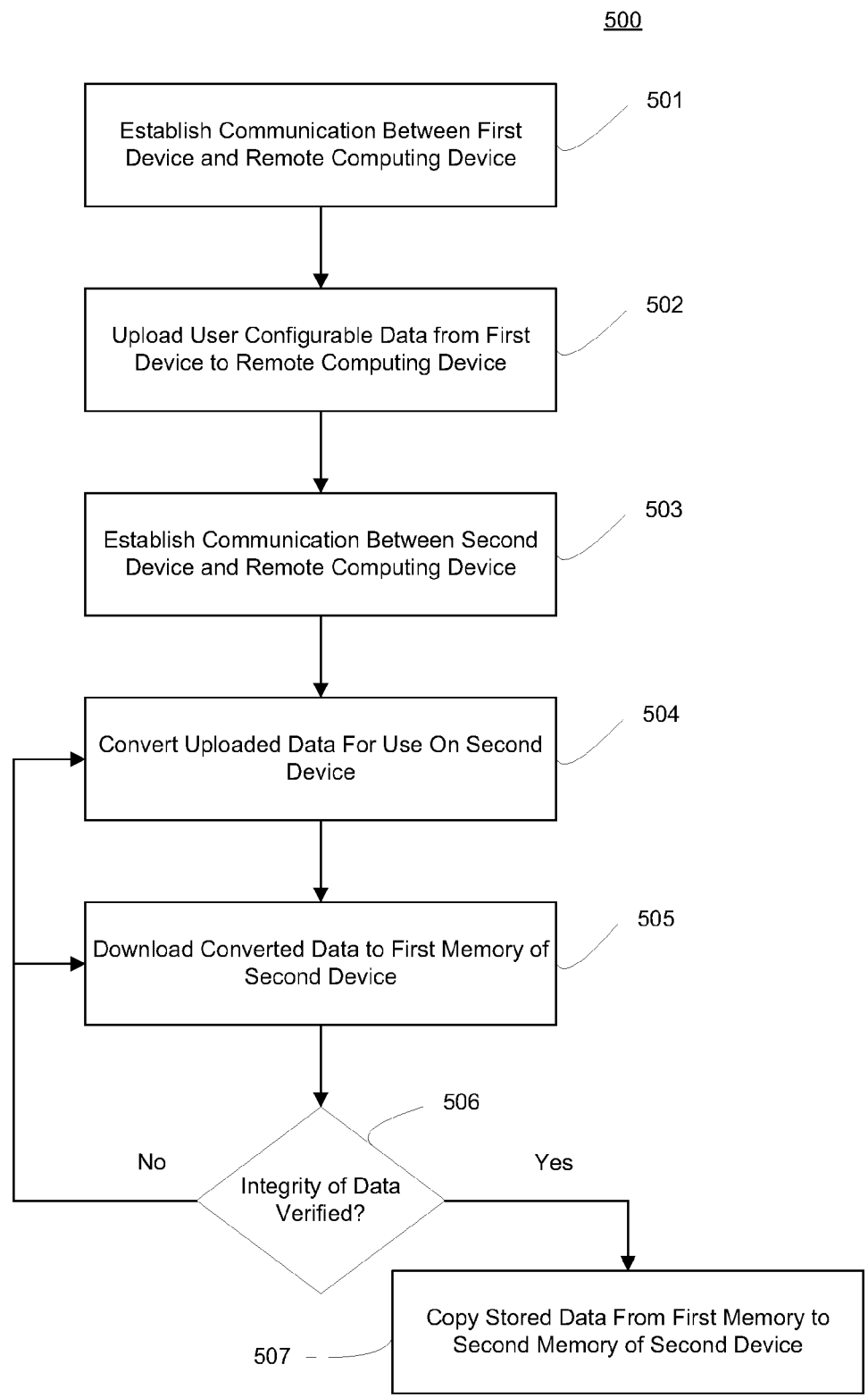
FIG. 5 is a flowchart illustrating a method for transferring user configurable data from a first device to a second device according to embodiments of the present disclosure.

FIG. 5 illustrates a method 500 for transferring user-configurable data from a first device to a second device according to embodiments of the present disclosure. The method 500 described herein may be used when the first device ceases to function or when use of another device is desired (e.g., when a physician prescribes use of a different device). In certain embodiments, the method 500 may be used to transfer data from the first device to the second device even if the devices are not related or have different functionality. For example, if the user is switching from a blood glucose monitoring device to a continuous glucose monitoring device, various settings from the blood glucose monitoring device may be transferred to the continuous glucose monitoring device. In another embodiment, the method 500 may be used to ensure that settings corresponding to user-configurable data and manufacturing data remain constant between various versions of software being executed on the device 201.

Referring to FIG. 5, electronic communication is established between the first device such as, for example, device 201 (FIG. 2) and a remote computing device (501). In certain embodiments, the connection may be a wired or wireless connection such as described above. In certain embodiments, when the communication link is established between the first device and the remote computing device, the first device may transmit an identifier, such as, for example, a serial number, to the remote computing device to identify the type of the first device, a manufacturer of the first device and/or a current software version being executed on the first device. In certain embodiments, a compatibility table, such as, for example compatibility table 600 (FIG. 6) may be used to identify the type of the first device, the manufacturer of the first device, and/or the software version being executed on the first device. In certain embodiments, a microprocessor of the first device causes this data to be sent automatically when the communication link between the first device and the remote computing device is established or in response to a request from the remote computing device.

When the first device has been identified, user-configurable data is packed (e.g. compressed) and uploaded from the first device to the remote computing device (502). In certain embodiments, the remote computing device is a server, such as, for example, server 203 (FIG. 2). In another embodiment, the remote computing device may be a personal computer, laptop, personal digital assistant, smart phone, tablet computer, or other such computing device.

In certain embodiments, the user-configurable data is uploaded from the first device to the remote computing device based on the user-configurable data that was most recently uploaded. For example, if some of the user-configurable data to be uploaded was recently uploaded to the server 203 (e.g. within a predetermined number of days in the past) and the user-configurable data has not been changed (e.g., the language setting of the first device has not been changed by the user), the user-configurable data is not uploaded again as it is duplicate data. In certain embodiments, if some of the data to be uploaded was received and/or stored on the first device prior to a threshold time limit (e.g., 6 months in the past) the data is not uploaded to the remote computing device.

Still referring to FIG. 5, once the user-configurable data from the first device has been uploaded to the remote computing device, electronic communication is established between the second device and the remote computing device (503). As discussed above, the electronic communication may be a wired or wireless connection. Further, the established communication between the second device and the remote server need not be direct but may be routed through other servers and/or various other devices. In certain embodiments, when a connection is established between the second device and the remote computing device, the second device may send either automatically, or in response to a request from the remote computing device, an identifier that may be used to identify the device and/or a current software version running on the device such as was described above.

When the second device has been identified (e.g. by a serial number of the second device), the data that was uploaded from the first device is converted for use on the second device (504). In certain embodiments, the user-configurable data is mapped by the remote computing device for use with the second device. Although a second device is specifically mentioned, it is contemplated that the data mapping described herein may also be used to map user-configurable data as well as non-user configurable data from a device that is transitioning from a first software version to a second software version.

In certain embodiments, the remote computing device maps the user-configurable data by changing the format of the user-configurable data from a first format that is compatible with the first device to a second format that is compatible with the second device, or from a format that is compatible with one software version to a second software version that is to be executed on the first device. For example, the user configurable data from the first device may correspond to threshold values, alarm settings, reminder settings, and language settings. The length of the data corresponding to the threshold values may be 2 bits, the length of the data corresponding to the alarm settings may be 2 bits, the length of the data corresponding to the reminder settings may be 4 bits and the length of the data corresponding to the language settings may be 4 bits.

As the data is mapped from the first device to the second device, the length of the data for each data element of the user-configurable data listed above may be changed by the remote computing device so the user-configurable data is compatible with the second device. Continuing with the above example, the length of the data for the threshold values may be changed to 4 bits, the length of the data for the alarm settings may remain at 2 bits, the length of the data for the reminder settings may be 6 bits, and the length of the data for the language settings may be 2 bits. Although the length of data element of the user-configurable data has been changed to be compatible with the second device, the actual setting represented by the data element remains unchanged. For example, if the language setting of the first device (represented by 4 bits) is English, when the length of the data corresponding to the language setting is changed from the first format (e.g., 4 bits in length) to the second format (e.g., 2 bits in length) the language setting represented by the second format is English.

If some of the user-configurable data from the first device is not used in the second device, the remote computing device disregards that particular data element of the user-configurable data. For example, if the first device has a data element corresponding to units of measure, and the second device does not have an equivalent setting, the data element of the user-configurable data corresponding to units of measure is disregarded during the mapping process.

Further, the second device may have user-configurable data corresponding to settings that were not supported by the first device. Thus, when the remote computing device maps the user-configurable data from the first device to the second device, the particular setting corresponding to the data element that is not supported by the first device will not have mapped user-configurable data. In such cases, the setting that does not have a corresponding data element is set as the factory default setting. The factory default setting may then be changed by the user. For example, the second device may have a unit of measure setting that allows the user to change the unit of measure from mg/dL to mMol/L while the first device did not have this setting. Thus, when user-configurable data is mapped, there is no data that corresponds to the unit of measure setting. As a result, the unit of measure setting will be set to default setting (e.g., mg/dL).

When the user-configurable data has been converted from the first format to the second format, the converted user-configurable data is downloaded and stored on the second device (505).

In certain embodiments, the converted user-configurable data is packed prior to being downloaded and stored on the second device and is stored in a first memory of the second device. In certain embodiments, the download operation may be performed by a software upgrade tool running on a computing device connected to the second device. In another embodiment, the remote computing device performs the download through client software running on a computing device that connects to the second device. In yet another embodiment, the software upgrade tool may be incorporated directly into the second device.

Referring back to FIG. 5, once the converted user-configurable data has been stored on the second device, the integrity of the converted user-configurable data is verified (506). The verification may be used to confirm that the converted user-configurable data is not corrupt and/or that if the user-configurable data was converted, the converted user-configurable data may be used by the second device. In certain embodiments, the verification is performed by cyclic redundancy check (CRC) such as described above. In another embodiment, the verification is performed by other error detection methods such as, for example, parity bits, checksums, cryptographic hash functions and the like.

In certain embodiments, when the converted user-configurable data stored on second device has been verified, the converted user-configurable data is copied from the first memory of the second device to a second memory of the second device (507). In certain embodiments, the first and/or second memory of the second device is random access memory. In another embodiment, the first memory of the second device is volatile memory and the second memory of the second device is non-volatile memory, which may be flash memory. In certain embodiments, the first memory and the second memory of the second device are non-volatile or flash memory.

In certain embodiments, the remote computing device may direct a computing device connected to the second device to perform the copying operation through client software running on the connected computing device. In other embodiments, the data copying may be performed on the second device itself without the need for further instructions from another computing device. When the converted user-configurable data has been copied to the second memory of the second device, the settings of the second device are based on the converted user-configurable data. Thus, when a user transitions from the first device to the second device, the user may immediately use the second device without having to manually adjust all of the settings in the second device. In certain embodiments, the second device continues to operate based on its previously-stored user-configurable data until further operations/instructions are performed in which the converted user-configurable data is needed by the second device.

Referring back to FIG. 5, if the converted user-configurable data is not verified (506), the user-configurable data that was uploaded from the first device is remapped for use with the second device (504). In certain embodiments, the remote computing device tracks the mapping of the user-configurable data and only remaps the user-configurable data that was not verified by the cyclic redundancy check. For example, if data corresponding to the language setting was correctly mapped but data corresponding to the threshold values was not correctly mapped, the server remaps the data corresponding to the threshold values. Once the user-configurable data has been mapped, the converted user-configurable data is downloaded to the first memory of the second device (505). The newly downloaded converted user-configurable data is then verified (506) and stored in the second memory of the second device if the converted user-configurable data is verified (507).

Although data mapping has been specifically described for mapping user-configurable data from a first device to a second device, it is contemplated that data mapping may be used to preserve user-configurable data from a first version of software being executed on the first device to a second version of the software (e.g. software upgrade) that is downloaded and installed on the first device.

According to the above-described embodiments, a user is advantageously able to recover device functionality from a remote computing device rather than replacing the device and/or manually inputting each user setting into the device. Further, the recovery may conveniently be done from the user's home or other preferred location. Moreover, recovery of the medical device provides a user access to a functioning medical device even if the software upgrade is unsuccessful.

FIG. 6 illustrates an exemplary compatibility table 600 according to embodiments of the present disclosure. In certain embodiments, the compatibility table is stored on a remote computing device, such as, for example, server 203 (FIG. 2). The remote computing device stores a compatibility table for each unique device, such as, for example, device 201 (FIG. 2). As discussed above, the compatibility table 600 for each device is identified by a serial number of the device 201, a partial serial number of the device 201 or other such identifier.

As shown in FIG. 6, the compatibility table 600 includes a history for each revision of software 610 for the device 201 as well as software/firmware revisions for the first microprocessor 620, the second microprocessor 630 and the third microprocessor 640 of the device 201. In certain embodiments, when an upgrade to the device 201 is performed, the details of the upgrade are stored in the compatibility table 600. Thus, as shown in FIG. 6, when the software of the device 201 was upgraded from Release 10 to Release 14, the software of the first microprocessor 620 of the device 201 was upgraded from Release 10 to Release 12, the software of the second microprocessor 630 was not upgraded and the software for the third microprocessor 640 was upgraded from Release 6 to Release 7.

In certain embodiments, the compatibility table 600 also includes information corresponding to persistent data (e.g., user-configurable data and manufacturing data) associated with each revision of the software of the device 610. Thus, although the user-configurable data may be mapped as described above with respect to FIG. 5, when the software of the device 201 is upgraded from Release 10 to Release 14, the user-configurable data associated with Release 10 of the software for the device 201 is stored on the remote computing device.

Referring back to FIG. 6, the compatibility table 600 also shows that the software 610 of device 201 was subsequently upgraded from Release 14 to Release 15. Although the software 610 of the device was upgraded, the software for each of the microprocessors 620, 630, and 640 were not upgraded.

In certain embodiments, the compatibility table 600 also stores information corresponding to a hardware version (not shown) of each of the microprocessors 620, 630 and 640 of the device 201. As will be explained below, when a software upgrade to the device 201 and/or one of the microprocessors 620, 630, or 640 is requested, the version of the hardware for the microprocessors is checked to determine if the desired software upgrade may be executed on hardware versions of the microprocessors 620, 630 and 640. If the microprocessors 620, 630 and 640 are not able to support the release required by the desired software version, the software upgrade will not be installed on the device 201.

Figure 7:
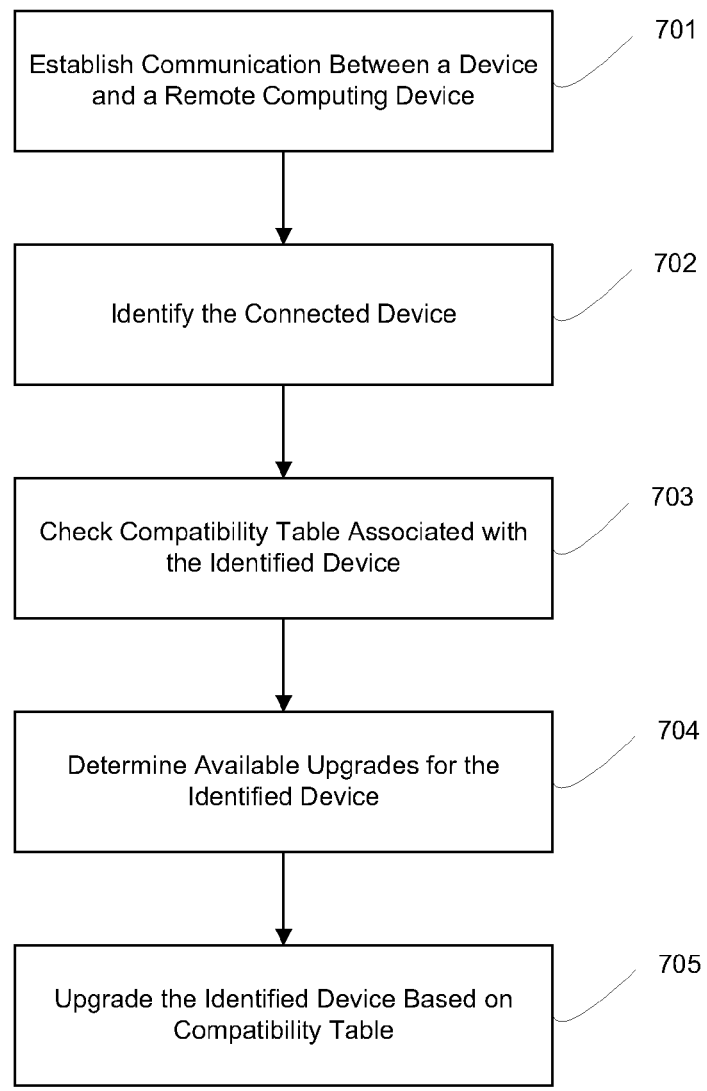
FIG. 7 is a flow chart illustrating a method for selectively upgrading a device based on a compatibility table according to embodiments of the present disclosure.

FIG. 7 is a flow chart illustrating a method 700 for selectively upgrading a device based on a compatibility table according to embodiments of the present disclosure. The routine for selectively upgrading the device, such as, for example device 201 (FIG. 2) begins when a communication link is established between the device 201 and a remote computing device (701). In certain embodiments, the communication link between the device 201 and the remote computing device, such as, for example, computing device 202 or server 203, is established through communication links 210 or 220. In one aspect, the communication link between the device 201 and the remote computing device is established using a wireless connection. In another aspect, the communication between the device 201 and the remote computing device is established using a wired connection such as, for example, by connecting the device 201 to the remote computing device using a USB cable.

In certain embodiments, when the device 201 is connected to a computing device 202, the computing device 202 is configured to execute an upgrade module to assist in transferring data from the server 203 to the device 201. In one aspect, the device 201 is configured to receive the upgrades directly from the server 203.

Once communication between the device 201 and the remote computing device is established, the remote computing device identifies the connected device 201 (702). In certain embodiments, the connected device 201 is identified using a serial number of the device 201, a partial serial number of the device 201, or other such identifier.

When the device 201 has been identified by the remote computing device, the compatibility table associated with the device 201 is checked to determine a version of the software currently being executed on the device 201 as well as the versions of software for each of the microprocessors of the device 201 (703). Once the software version of the device 201 is identified, available upgrades for the device 201 are determined (704). In certain embodiments, the remote computing device stores all available upgrades for the various devices. When determining available upgrades for an identified device 201, a processor of the remote computing device compares a current version of the software and/or firmware of the device 201 from the compatibility table to available software and firmware upgrades.

If an upgrade is available, the compatibility table associated with the device 201 is checked by the processor of the remote computing device to determine which components of the device 201 need to be upgraded. Only the components of the device 201 that need to be upgraded to support the new version of the software are upgraded (705). For example, if the identified device 201 is executing Release 10 of the software 610 (FIG. 6) and the available upgrade is software Release 14, when the software 610 for the device 201 is upgraded, software for the first microprocessor 620 is upgraded from Release 10 to Release 12, and software for the third microprocessor 640 is upgraded from Release 6 to Release 7. As shown in the compatibility table 600, Release 14 of the software 610 does not require that the second microprocessor 630 be upgraded. As such, only the required data for the upgrade is downloaded and installed on the device 201. In certain embodiments, the device 201 and the microprocessors of the device 201 are upgraded using the method 300 described above with respect to FIG. 3. Additionally, the user-configurable settings of the device 201 may be mapped from Release 10 of the software 610 of the device 201 to Release 14 of the software 610 of the device 201 according to the method 500 described above with respect to FIG. 5.

In certain embodiments, prior to upgrading the software of the device 201, a processor of the remote computing device determines a hardware version of each of the microprocessors of the device 201 and further determines whether the hardware version of each of the microprocessors can execute the software release required to run the new version of the software for the device 201. If the hardware version of the microprocessors cannot execute the required software release version, the software upgrade for the device 201 will not be installed on the device 201.

For example, as shown in the compatibility table 600, Release 15 of the software 610 requires that the first microprocessor 620 execute Release 12 version of the software, the second microprocessor 630 execute Release 8 version of the software, and the third microprocessor 640 execute Release 7 version of the software. If however, the hardware version of the first microprocessor 620 cannot execute Release 12 version of the software, the Release 15 version of the software 610 will not be installed on the device 201.

In certain embodiments, the current version of the bootloader of the device 201 may also be stored in a compatibility table associated with the device 201. As available software upgrades for the device 201 and each of the microprocessors of the device are determined, available upgrades for the bootloader of the device 201 may also be determined. If upgrades to the bootloader are available, the bootloader is upgraded along with the software version of the device 201 and/or the microprocessors of the device 201.

Figure 8:
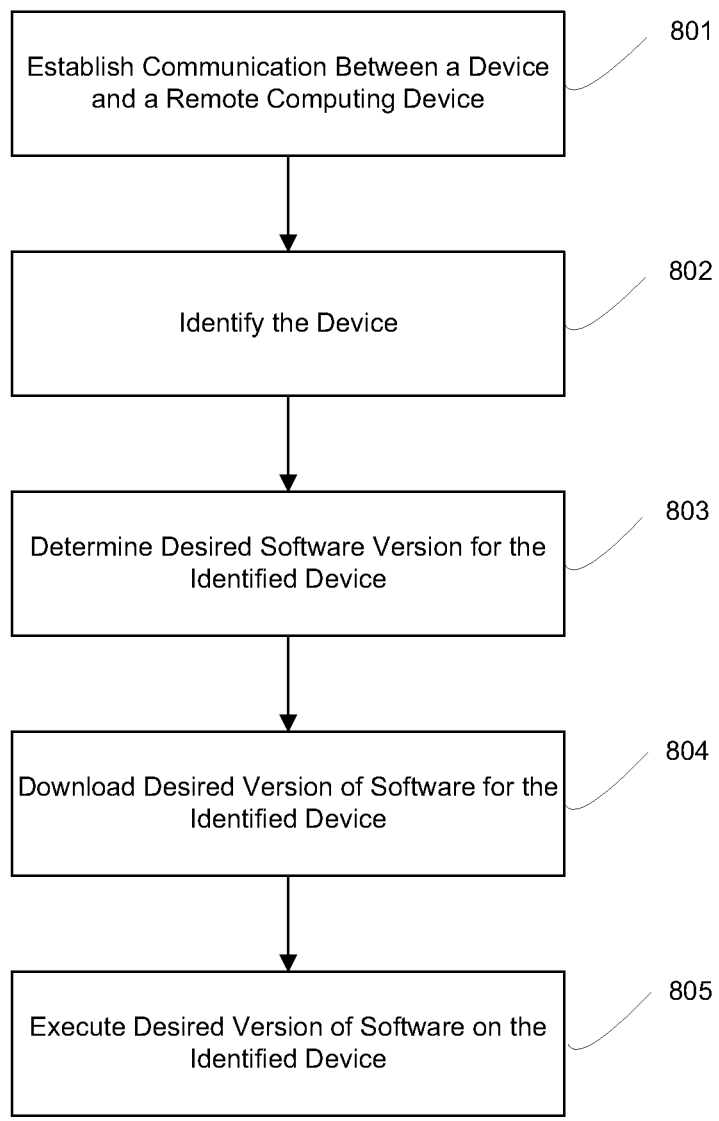
FIG. 8 is a flow chart illustrating a method for reverting to a previous version of software for a device according to embodiments of the present disclosure.

FIG. 8 is a flow chart illustrating a method 800 for reverting to a previous version of software for a device according to embodiments of the present disclosure. In certain embodiments, the method 800 described with reference to FIG. 8 may be used to restore functionality to a device, such as, for example device 201 (FIG. 2) when the device 201 has lost manufacturing settings (e.g., the device 201 is a dead device) or when a user upgraded the software on the device 201 and wishes to revert to a software version that was previously installed on the device 201 (e.g., the version of the software that was installed on the device 201 prior to the upgrade being installed on the device 201).

The routine for reverting to a previous version of software for the device 201 begins when a communication link is established between the device 201 and a remote computing device (801). In certain embodiments, the communication link between the device 201 and the remote computing device, such as, for example, computing device 202 or server 203, is established through communication links 210 or 220. In one aspect, the communication link between the device 201 and the remote computing device is established using a wireless connection. In another aspect, the communication link between the device 201 and the remote computing device is established using a wired connection such as, for example, by connecting the device 201 to the remote computing device using a USB cable.

In certain embodiments, when the device 201 is connected to a computing device 202, the computing device 202 is configured to execute an upgrade module configured to transfer reversion data (e.g., data corresponding to the previously installed software version) from the server 203 to the device 201. In one aspect, the device 201 is configured to receive the reversion data directly from the server 203.

Once communication between the device 201 and the remote computing device is established, the remote computing device identifies the connected device 201 (802). In certain embodiments, the connected device 201 is identified using a serial number of the device 201, a partial serial number of the device 201, or other such identifier. In situations where the device 201 is being recovered from being dead (e.g., manufacturing data of the device 201 is lost) the user may need to manually identify the device 201 such as, for example, by manually inputting a serial number or partial serial number of the device 201 into a user interface provided on the remote computing device. In certain embodiments, a user may contact customer service of the manufacturer of the device and provide the serial number of the device 201 to a customer service representative.

Once the device 201 has been identified, a desired software version for the identified device 201 is determined (803). In certain embodiments, the determination of the desired software version of the identified device 201 is made by a user manually selecting a previous version of software for the device 201 from a compatibility table, such as, for example compatibility table 600 (FIG. 6). In another embodiment, the customer service representative may use the serial number of the device 201 to access the compatibility table corresponding to the device 201 and transmit the desired software version of the device 201 to the user. In another embodiment, a processor of the remote computing device identifies the most recent software version that was stored on the device and transmits the latest version of the software and associated data to the device 201. For example, when the device 201 is being recovered from being dead, the desired software version may correspond to the latest software version stored in the compatibility table 600 (e.g., Release 15 of the software 610). Thus, Release 15 of the software 610, and the corresponding user-configurable settings and/or manufacturing settings, are transmitted to the device 201. Although the latest version of the software is specifically mentioned, it is contemplated that any previous version of software stored in the compatibility table 600 may be identified and transmitted to the device 201 when recovering a dead device or when reverting to a previous version of software for the device 201.

When the desired software version of the identified device 201 is determined, the desired version of the software of the device 201, including the associated manufacturing settings and user-configurable settings of the device 201, are downloaded and stored on the identified device 201 (804). In certain embodiments, the desired version of software for the device 201 is downloaded to the identified device 201 using the method 300 described above with reference to FIG. 3. If the desired version of the software for the identified device 201 requires that user-configurable settings be mapped from the current version of the software being executed on the device 201 to the desired version of the software for the device, the user-configurable data is mapped according to the method 500 described above with reference to FIG. 5. Once the desired version of the software of the device 201 has been downloaded to the identified device 201, the desired version of the software of the device 201 is executed by a microprocessor of the identified device 201 (805).

If the device 201 is recovering from being a dead device, a desired version of the software of the identified device 201, including the manufacturing settings and user-configurable settings of the device 201, are loaded on a bootloader of the device 201 (e.g., either directly from a server or through a connection to a computing device). When the device 201 boots, the bootloader of the device 201 loads and executes the desired version of the software for the identified device 201 (805) including the corresponding software for each of the microprocessors of the device 201. Once the device 201 has recovered from being dead using the bootloader, the desired version of the software, along with the manufacturing settings and user-configurable settings of the device 201 associated with the desired version of the software, are stored in a memory of the device 201.

One aspect of the present disclosure includes establishing a connection between a medical device and a remote computing device; receiving an upgrade command at the medical device; storing a current version of persistent data and a current version of executable code in a first storage area of the medical device; transmitting at least the current version of the persistent data to the remote computing device, wherein the remote computing device is configured to convert the current version of the persistent data from a first format to a second format; receiving the second format of the current version of the persistent data and an upgraded version of executable code at the medical device; storing the second format of the current version of the persistent data and the upgraded version of the executable code in a second storage area of the medical device; and executing the upgraded version of the executable code with the second format of the current version of the persistent data.

One embodiment further includes verifying the integrity of the upgraded version of the executable code and the second format of the current version of the persistent data prior to executing the upgraded version of the executable code.

Moreover, in one embodiment, the integrity of the upgraded version of the executable code and the second format of the current version of the persistent data is verified using a cyclic redundancy check.

In another embodiment, converting the current version of the persistent data from the first format to the second format includes modifying the layout of the data associated with the current version of the persistent data.

Another embodiment further includes copying the upgraded executable code and the second format of the current version of the persistent data from the second storage area to the first storage area.

In another embodiment, the current version of the persistent data is one or more of user-configurable data or manufacturing data.

Yet another embodiment includes executing the current version of executable code with the current version of the persistent data when an error associated with the upgraded version of the executable code or the second format of the current version of the persistent data is detected.

In another aspect, an apparatus includes one or more processors; and a memory for storing instructions which, when executed by the one or more processors, causes the one or more processors to establish a connection to a remote computing device, receive an upgrade command, store a current version of persistent data and a current version of executable code in a first storage area of the memory, transmit at least the current version of the persistent data to the remote computing device, wherein the remote computing device is configured to convert the current version of the persistent data from a first format to a second format, receive the second format of the current version of the persistent data and an upgraded version of executable code, store the second format of the current version of the persistent data and the upgraded version of the executable code in a second storage area of the memory, and execute the upgraded version of the executable code with the second format of the current version of the persistent data.

Another aspect of the present disclosure includes establishing a connection between a first medical device and a remote computing device; storing user-configurable data associated with the first medical device on the remote computing device; establishing a connection between a second medical device and the remote computing device; converting the user-configurable data associated with the first medical device from a first format to a second format, wherein the second format of the user-configurable data corresponds to the second medical device; and transmitting the second format of the user-configurable data to the second medical device, wherein the second format of the user-configurable data is configured to alter at least one setting of the second medical device.

In one embodiment, converting the user-configurable data associated with the first medical device from a first format to a second format includes changing the layout of the user-configurable data.

In another embodiment, changing the layout of the user-configurable data includes altering a number of bits of each data element associated with the user-configurable data.

Another embodiment includes verifying the integrity of the second format of the user-configurable data prior to altering at least one setting of the second medical device based on the second format of the user-configurable data.

Moreover, in one embodiment, the integrity of the second format of the user-configurable data is verified using a cyclic redundancy check.

In one aspect, a system includes a remote computing device; a first medical device in signal communication with the remote computing device; and a second medical device in signal communication with the remote computing device; wherein the remote computing device is configured to store user-configurable data associated with the first medical device; convert the user-configurable data associated with the first medical device from a first format to a second format, wherein the second format of the user-configurable data corresponds to the second medical device; and transmit the second format of the user-configurable data to the second medical device, wherein the second format of the user-configurable data is configured to alter at least one setting of the second medical device.

Another aspect of the present disclosure includes establishing a connection between a medical device and a remote computing device; identifying the medical device; comparing a current version of software of the medical device with one or more available versions of software for the medical device using a compatibility table, wherein the compatibility table is associated with the identified medical device; and transmitting an available version of the software for the medical device to the medical device.

One embodiment includes selectively transmitting a plurality of the available versions of software to the medical device based on the compatibility table.

In another embodiment, one or more of the available one or more versions of software for the medical device includes firmware.

In yet another embodiment, the available one or more versions of software for the medical device includes software for one or more processors of the medical device.

In another embodiment, the available one or more versions of software for the medical device includes firmware for one or more processors of the medical device.

In yet still another embodiment, the available one or more versions of software for the medical device are based, at least in part, on a hardware version of at least one component of the medical device.

Moreover, in one embodiment, the hardware version of the at least one component of the medical device is stored in the compatibility table.

In another embodiment, the medical device is identified by a serial number of the medical device.

In another aspect of the present disclosure, an apparatus includes one or more processors; and a memory for storing instructions which when executed by the one or more processors, causes the one or more processors to establish a connection to a medical device, identify the medical device, compare a current version of software of the medical device with one or more available versions of software for the medical device using a compatibility table, wherein the compatibility table is associated with the identified medical device, and transmit an available version of the software for the medical device to the medical device.

Another aspect includes establishing a connection between a medical device and a remote computing device; identifying the medical device; receiving a request for data corresponding to at least one of a version of persistent data for the medical device or a version of executable code for the medical device; identifying the requested data based at least in part on a compatibility table; and transmitting the identified data corresponding to the at least one of the version of persistent data for the medical device or the version of executable code for the medical device.

In one embodiment, the medical device is identified by a serial number of the medical device.

In another embodiment, the compatibility table is identified based on the serial number of the medical device.

In yet another embodiment, the version of the persistent data corresponds to at least one of user-selectable data or manufacturing data.

In still another embodiment, the version of the persistent data is configured to replace persistent data stored on the medical device.

In another embodiment, the version of the executable code for the medical device is configured to replace executable code stored on the medical device.

In another aspect of the present disclosure, an apparatus includes one or more processors; and a memory for storing instructions which, when executed by the one or more processors, causes the one or more processors to establish a connection between a medical device and a remote computing device, identify the medical device, receive a request for data corresponding to at least one of a version of persistent data for the medical device or a version of executable code for the medical device, identify the requested data based at least in part on a compatibility table, and transmit the identified data corresponding to the at least one of the version of persistent data for the medical device or the version of executable code for the medical device.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A method comprising:
  establishing a connection between a medical device and a remote computing device;
  receiving an upgrade command at the medical device;
  storing a current version of persistent data and a current version of executable code in a first storage area of the medical device;
  transmitting at least the current version of the persistent data to the remote computing device, wherein the remote computing device is configured to convert the current version of the persistent data from a first format to a second format;
  receiving the second format of the current version of the persistent data and an upgraded version of executable code at the medical device;
  storing the second format of the current version of the persistent data and the upgraded version of the executable code in a second storage area of the medical device;
  executing the upgraded version of the executable code with the second format of the current version of the persistent data;
  detecting a failure of a critical component of the upgraded version of the executable code; and
  disabling the functionality of the medical device related to the critical component of the upgraded version of the executable code when the failure is detected.

2. The method of claim 1, further comprising verifying an integrity of the upgraded version of the executable code and the second format of the current version of the persistent data prior to executing the upgraded version of the executable code.

3. The method of claim 2, wherein the integrity of the upgraded version of the executable code and the second format of the current version of the persistent data is verified using a cyclic redundancy check.

4. The method of claim 1, wherein converting the current version of the persistent data from the first format to the second format includes modifying a layout of the data associated with the current version of the persistent data.

5. The method of claim 1, further comprising copying the upgraded executable code and the second format of the current version of the persistent data from the second storage area to the first storage area.

6. The method of claim 1, wherein the current version of the persistent data is one or more of user-configurable data or manufacturing data.

7. The method of claim 1, further comprising executing the current version of executable code with the current version of the persistent data when an error associated with a non-critical component of the upgraded version of the executable code or the second format of the current version of the persistent data is detected.

8. An apparatus, comprising:
  one or more processors; and
  a memory for storing instructions which, when executed by the one or more processors, causes the one or more processors to establish a connection to a remote computing device, receive an upgrade command, store a current version of persistent data and a current version of executable code in a first storage area of the memory, transmit at least the current version of the persistent data to the remote computing device, wherein the remote computing device is configured to convert the current version of the persistent data from a first format to a second format, receive the second format of the current version of the persistent data and an upgraded version of executable code, store the second format of the current version of the persistent data and the upgraded version of the executable code in a second storage area of the memory, execute the upgraded version of the executable code with the second format of the current version of the persistent data, detect a failure of a critical component of the upgraded version of the executable code, and disable a functionality of the apparatus related to the critical component of the upgraded version of the executable code when the failure is detected.

9. The apparatus of claim 8, wherein the memory for storing instructions which, when executed by the one or more processors, causes the one or more processors to verify an integrity of the upgraded version of the executable code and the second format of the current version of the persistent data prior to executing the upgraded version of the executable code.

10. The apparatus of claim 9, wherein the integrity of the upgraded version of the executable code and the second format of the current version of the persistent data is verified using a cyclic redundancy check.

11. The apparatus of claim 8, wherein converting the current version of the persistent data from the first format to the second format includes modifying a layout of the data associated with the current version of the persistent data.

12. The apparatus of claim 8, wherein the memory for storing instructions which, when executed by the one or more processors, causes the one or more processors to copy the upgraded version of the executable code and the second format of the current version of the persistent data from the second storage area to the first storage area.

13. The apparatus of claim 8, wherein the current version of the persistent data is one or more of user-configurable data or manufacturing data.

14. The apparatus of claim 8, wherein the memory for storing instructions which, when executed by the one or more processors, causes the one or more processors to execute the current version of executable code with the current version of the persistent data when an error associated with a non-critical component of the upgraded version of the executable code or the second format of the current version of the persistent data is detected.

15. A method comprising:
establishing a connection between a first medical device and a remote computing device;
storing user-configurable data associated with the first medical device on the remote computing device;
establishing a connection between a second medical device and the remote computing device;
converting the user-configurable data associated with the first medical device from a first format to a second format, wherein the second format of the user-configurable data corresponds to the second medical device; and
transmitting the second format of the user-configurable data to the second medical device, wherein the second format of the user-configurable data is configured to alter at least one setting of the second medical device;
wherein the first medical device is a blood glucose monitoring device and the second medical device is a continuous glucose monitoring device.

16. The method of claim 15, wherein converting the user-configurable data associated with the first medical device from the first format to the second format includes changing a layout of the user-configurable data.

17. The method of claim 16, wherein changing the layout of the user-configurable data includes altering a number of bits of each data element associated with the user-configurable data.

18. The method of claim 15, further comprising, verifying an integrity of the second format of the user-configurable data prior to altering at least one setting of the second medical device based on the second format of the user-configurable data.

19. The method of claim 18, wherein the integrity of the second format of the user-configurable data is verified using a cyclic redundancy check.

20. A system, comprising:
a remote computing device;
a first medical device in signal communication with the remote computing device; and
a second medical device in signal communication with the remote computing device;
wherein the remote computing device is configured to:
store user-configurable data associated with the first medical device;
convert the user-configurable data associated with the first medical device from a first format to a second format, wherein the second format of the user-configurable data corresponds to the second medical device; and
transmit the second format of the user-configurable data to the second medical device, wherein the second format of the user-configurable data is configured to alter at least one setting of the second medical device;
wherein the first medical device is a blood glucose monitoring device and the second medical device is a continuous glucose monitoring device.

21. The system of claim 20, wherein converting the user-configurable data associated with the first medical device from the first format to the second format includes changing a layout of the user-configurable data.

22. The system of claim 21, wherein changing the layout of the user-configurable data includes altering a number of bits of each data element associated with the user-configurable data.

23. The system of claim 20, wherein the second medical device is configured to verify an integrity of the second format of the user-configurable data prior to altering at least one setting based on the second format of the user-configurable data.

24. The system of claim 21, wherein the integrity of the second format of the user-configurable data is verified using a cyclic redundancy check.

25. A method comprising:
establishing a connection between a medical device and a remote computing device;
identifying the medical device;
comparing a current version of software of the medical device with one or more available versions of software for the identified medical device using a compatibility table, wherein the compatibility table is associated with the identified medical device; and
transmitting an available version of the software for the identified medical device to the identified medical device;
wherein the transmitted available version of the software for the identified medical device includes a bolus calculation function of the identified medical device or a bolus delivery function of a peripheral pump operatively connected to the identified medical device.

26. The method of claim 25, further comprising selectively transmitting a plurality of the available versions of software to the identified medical device based on the compatibility table.

27. The method of claim 25, wherein the available one or more versions of software for the identified medical device includes software for one or more processors of the identified medical device.

28. The method of claim 25, wherein the available one or more versions of software for the identified medical device includes firmware for one or more processors of the identified medical device.

29. The method of claim 25, wherein the available one or more versions of software for the identified medical device are based, at least in part, on a hardware version of at least one component of the identified medical device.

30. The method of claim 29, wherein the hardware version of the at least one component of the identified medical device is stored in the compatibility table.

31. The method of claim 25, wherein the medical device is identified by a serial number of the medical device.

32. An apparatus, comprising:
one or more processors; and
a memory for storing instructions which when executed by the one or more processors, causes the one or more processors to establish a connection to a medical device, identify the medical device, compare a current version of software of the identified medical device with one or more available versions of software for the medical device using a compatibility table, wherein the compatibility table is associated with the identified medical device, and transmit an available version of the software for the identified medical device to the identified medical device, wherein the transmitted available version of the software for the identified medical device includes a bolus calculation function of the identified medical device or a bolus delivery function of a peripheral pump operatively connected to the identified medical device.

33. The apparatus of claim 32, wherein the memory for storing instructions which, when executed by the one or more processors, causes the one or more processors to selectively transmit a plurality of available versions of software to the identified medical device based on the compatibility table.

34. The apparatus of claim 32, wherein the one or more available versions of software for the identified medical device includes software for the one or more processors of the identified medical device.

35. The apparatus of claim 32, wherein the one or more available versions of software for the identified medical device includes firmware for the one or more processors of the identified medical device.

36. The apparatus of claim 32, wherein the available one or more versions of software for the identified medical device are based, at least in part, on a hardware version of at least one component of the identified medical device.

37. The apparatus of claim 36, wherein the hardware version of the at least one component of the identified medical device is stored in the compatibility table.

38. The apparatus of claim 32, wherein the medical device is identified by a serial number of the medical device.

39. A method comprising:
establishing a connection between a medical device and a remote computing device;
identifying the medical device;
receiving a request for data corresponding to at least one of a version of persistent data for the medical device or a version of executable code for the medical device;
identifying the requested data based at least in part on a compatibility table; and
transmitting the identified data corresponding to the at least one of the version of persistent data for the medical device or the version of executable code for the medical device;
wherein the transmitted identified data corresponding to the at least one of the version of persistent data for the medical device or the version of executable code for the medical device includes a bolus calculation function of the medical device or a bolus delivery function of a peripheral pump operatively connected to the medical device.

40. The method of claim 39, wherein the medical device is identified by a serial number of the medical device.

41. The method of claim 40, wherein the compatibility table is identified based on the serial number of the medical device.

42. The method of claim 39, wherein the version of the persistent data corresponds to at least one of user-selectable data or manufacturing data.

43. The method of claim 39, wherein the version of the persistent data is configured to replace persistent data stored on the medical device.

44. The method of claim 39, wherein the version of the executable code for the medical device is configured to replace executable code stored on the medical device.

45. An apparatus, comprising:
one or more processors; and
a memory for storing instructions which, when executed by the one or more processors, causes the one or more processors to establish a connection between a medical device and a remote computing device, identify the medical device, receive a request for data corresponding to at least one of a version of persistent data for the medical device or a version of executable code for the medical device, identify the requested data based at least in part on a compatibility table, and transmit the identified data corresponding to the at least one of the version of persistent data for the medical device or the version of executable code for the medical device, wherein the transmitted identified data corresponding to the at least one of the version of persistent data for the medical device or the version of executable code for the medical device includes a bolus calculation function of the medical device or a bolus delivery function of a peripheral pump operatively connected to the medical device.

46. The apparatus of claim 45, wherein the medical device is identified by a serial number of the medical device.

47. The apparatus of claim 46, wherein the compatibility table is identified based on the serial number of the medical device.

48. The apparatus of claim 45, wherein the version of the persistent data corresponds to at least one of user-selectable data or manufacturing data.

49. The apparatus of claim 45, wherein the version of the persistent data is configured to replace persistent data stored on the medical device.

50. The apparatus of claim 45, wherein the version of the executable code for the medical device is configured to replace executable code stored on the medical device.

51. The method of claim 1, wherein the critical component of the upgraded version of the executable code is related to a bolus calculation function of the medical device or a bolus delivery function of a peripheral pump operatively connected to the medical device.

52. The apparatus of claim 8, wherein the critical component of the upgraded version of the executable code is related to a bolus calculation function of the apparatus or a bolus delivery function of a peripheral pump operatively connected to the apparatus.

* * * * *